United States Patent [19]
Chervitz et al.

[11] Patent Number: 5,688,284
[45] Date of Patent: Nov. 18, 1997

[54] VARIABLE ANGLE DRILL GUIDE AND LIGAMENT FIXATION METHOD

[75] Inventors: Alan Chervitz; E. Marlowe Goble, both of Logan, Utah

[73] Assignee: MedicineLodge, Inc., Logan, Utah

[21] Appl. No.: 717,012

[22] Filed: Sep. 20, 1996

[51] Int. Cl.$^6$ .................................................. A61B 17/17
[52] U.S. Cl. ...................... 606/96; 606/86; 606/88; 606/102
[58] Field of Search .................. 606/79, 80, 86–88, 606/96–98, 102, 104

[56] References Cited

U.S. PATENT DOCUMENTS

| | | | |
|---|---|---|---|
| 4,257,411 | 3/1981 | Cho | 606/96 |
| 4,535,768 | 8/1985 | Hourahane et al. | 606/86 |
| 4,668,233 | 5/1987 | Seedhom et al. | 623/13 |
| 4,672,957 | 6/1987 | Hourahane et al. | 606/80 |
| 4,739,751 | 4/1988 | Sapega et al. | 606/96 |
| 4,823,780 | 4/1989 | Odensten et al. | 606/96 |
| 4,901,711 | 2/1990 | Goble et al. | 606/98 |
| 4,920,958 | 5/1990 | Walt et al. | 606/96 |
| 4,985,032 | 1/1991 | Goble | 606/96 |
| 5,152,764 | 10/1992 | Goble | 606/96 |
| 5,234,434 | 8/1993 | Goble | 606/96 |
| 5,314,429 | 5/1994 | Goble | 606/96 |
| 5,385,567 | 1/1995 | Goble | 606/96 |

FOREIGN PATENT DOCUMENTS

0126520 11/1984 European Pat. Off. .
2078528 1/1982 United Kingdom .

Primary Examiner—Michael Buiz
Assistant Examiner—David O. Reip
Attorney, Agent, or Firm—M. Reid Russell

[57] ABSTRACT

A variable angle drill guide and method for its use for securing an end of a ligament graft in a tunnel section of a straight tunnel section that has been formed into a patient's knee in a procedure for replacing a cruciate ligament. The drill guide includes a straight reference rod that is for fitting to slide through a straight hole formed in a slide block and includes a crossing straight hole that is for receiving, fitted therethrough, a straight base leg rod that is bent from one end into a straight drill guide mounting leg, the mount leg, in turn, to mount an arcuate shaped slide track along its top end. The slide track is curved to approximately one hundred twenty (120) degrees of arc and is arranged to maintain a drill guide slide traveling therealong that includes a drill guide barrel that is fitted to slide therethrough. By adjusting and locking positioning of the reference rod and base leg rod fitted through the slide block, the drill guide barrel will point at a target depression formed in the reference rod, whereby a drill turned through the drill guide barrel will form a passage from any point on the frontal cortex of the distal femur or proximal tibia to the target depression, formed in the reference rod. This formed passage will be at an angle to the tunnel section that is greater or lesser than a right angle and, upon removal of the reference rod and installation of a ligament graft in the straight tunnel, the formed passage can receive a screw turned therein to contact the ligament graft end, for mounting it in the tunnel section.

15 Claims, 5 Drawing Sheets

VARIABLE ANGLE DRILL GUIDE AND LIGAMENT FIXATION METHOD

BACKGROUND OF THE INVENTION

1. Field of the Invention

This invention relates to surgical devices and in particular to drill guides as are used in arthroscopic surgical procedures for knee reconstruction for drilling one or more holes to intersect at a point or points along a tibial or femoral tunnel as have been formed into a patient's knee and pass through the ligament points of origin.

PRIOR ART

The invention, like a number of earlier drill guides of one or both of the inventors, is preferably for use in an anterior or posterior cruciate ligament repair and/or replacement surgical procedure where tibial and femoral tunnel sections are formed in the distal femur and proximal tibia that pass through the ligament points of origin. Which tibial and femoral tunnel sections, with the knee bent appropriately, are straight. The tunnel sections are referenced by the respective drill guides for drilling holes from the distal femur and/or proximal tibia surfaces to intersect the tunnel or tunnels. Such intersecting holes can be used for passing an interference mounting device, such as a screw, therethrough to maintain a ligament end endosteally secured in a tunnel section. Earlier drill guides of one of the inventors are shown in U.S. Pat. No. 4,901,711; in U.S. Pat. No. 4,985,032; in U.S. Pat. No. 5,152,764; and in U.S. Pat. No. 5,234,434. All of which earlier drill guides, however, provide only for drilling a hole or holes to intersect a reference tunnel at an angle of ninety (90) degrees. Whereas, the drill guide of the present invention is for drilling holes from the tibial or femoral cortex to intersect a selected location along a reference tunnel at an angle that is less than or greater than ninety (90) degrees.

The drill guides set out above are for forming right angle passages or holes only to a point along a ligament mounting tunnel or tunnels. Additionally, a number of earlier drill guides have been used in knee arthroscopic surgical procedures for drilling, from without the knee, to a locator point within the knee intra articular joint. Examples of such earlier drill guides are shown in patents to Walt, et al, U.S. Pat. No. 4,920,958; to Sapega, et al, U.S. Pat. No. 4,739,751; to Cho, U.S. Pat. No. 4,257,411; to Hourahane, et al, U.S. Pat. No. 4,535,768; to Hourahane, et al, U.S. Pat. No. 4,672,957; and a United Kingdom Patent to Lovell, et al, No. 2,078,528. Also, while other earlier drilling devices have been developed for drilling tibial and femoral tunnel sections, none have provided for drilling or forming intersecting holes or passages to a select location or locations along tunnel sections at angles over a range of angles that is greater and lesser than ninety (90) degrees. Examples of such devices are shown in patents to Odensten, et al, U.S. Pat. No. 4,823,780; to Seedholm, et al, U.S. Pat. No. 4,668,233; and in a European Patent Application No. 0126520.

Most of the above cited references show devices for drilling to locations within a knee joint, so as to form right angle holes to intersect tibial and femoral tunnel sections that have already been formed therein. Whereas, the cited Hourahane, et al., and Hourahane patents, U.S. Pat. Nos. 4,535,768 and 4,672,957, provide a device that could conceivably be used to drill to a tunnel section location at less than a right angle. Similarly, U.S. patents to one of the inventors, U.S. Pat. Nos. 5,314,429 and 5,385,567, also show a device and method for its use for forming a straight passage to a tunnel section to intersect a location therealong at less than a right angle. None of which Hourahane and earlier patents of one of the inventors, however, provide a device that is structurally and functionally like that of the invention and method for its use that is used to easily and conveniently drill a straight passage to intersect a tunnel section location, which drilling is at an angle less than or greater than a right angle from a selected location over most of the tibial and femoral cortex surfaces, intersecting a location within a femoral and tibial tunnel section.

SUMMARY OF THE INVENTION

It is a principal object of the present invention in a variable angle drill guide to provide a device for fitting in so as to reference aligned straight femoral and tibial tunnel sections that are formed in a patient's bent knee, which drill guide can be positioned for guiding drilling of a straight passage from a selected point on the distal femur or proximal tibia cortex surfaces to intersect a selected point along one of the femoral or tibial tunnels sections, which passage is formed at an angle that is less than or greater than a right angle to the selected point or location in the selected tunnel section.

Another object of the present invention is to provide a variable angle drill guide having a capability for setting a desired angle for drilling, at a greater or lesser angle than a right angle, to a point or location on a reference rod.

Another object or the present invention is to provide a variable angle drill guide that provides for positioning a barrel thereof that a drill is fitted through so as to exactly drill a hole from a location on a distal femur or proximal tibia surface to a target point on the reference rod with that reference rod have been installed in a femoral or tibial tunnel section, the drill to form a passage that is at an angle greater or lesser than a right angle.

Another object of the present invention is to provide a variable angle drill guide that gives a surgeon/operator the capability for selecting different locations along a femoral or tibial tunnel section to form a hole or passage to by a setting of the drill guide components to drill such hole that is at an angle that is greater or lesser than a right angle.

Still another object of the present invention is to provide a variable angle drill guide that is easily positioned and repositioned to guide drilling of a straight hole to intersect a selected point that is at an angle that is greater or lesser than a right angle.

Still another object of the present invention is to provide a variable angle drill guide that includes calibrations scribed along reference rod and base leg members that cross one another in a slide block, for setting positioning of the crossing members to enable drilling of a passage to one of a number of potential locations along a femoral or tibial tunnel section, the device further providing for setting the angle of a drill guide barrel wherethrough the drill is turned to form a passage at an angle that is less than or greater than a right angle from a location on the tibial or femoral surface to a selected location in the tunnel section.

Still another object of the present invention is to provide a variable angle drill guide that is versatile, reliable and easy to use by a surgeon/operator performing a cruciate ligament repair or replacement surgical procedure.

The variable angle drill guide of the invention is for guiding drilling of a straight tunnel or passage from a location on a frontal portion of a distal femur or proximal tibia cortex surface to intersect, at an angle greater or lesser than a right angle, a point or location selected along a tibial or femoral tunnel section that a reference rod of the drill guide is positioned in. The drilled passage is for fitting a connector therethrough that is preferably for mounting a natural or prosthetic ligament end in that tunnel section. The invention includes the straight reference rod that is, prior to positioning in the femoral or tibial tunnel section, fitted through a slide block wherethrough a straight base leg of a drill guide brace is previously fitted. The respective reference rod and straight base leg thereby cross one another in the slide block, and will each slide back and forth therein. The drill guide brace from the straight base leg is bent through a right angle to a straight guide mounting leg. A top end of the guide mounting leg is secured to an end of an arcuate slide track such that the straight guide mounting leg and arcuate slide track are in the same plane, with the accurate slide track curved through approximately one hundred twenty (120) degrees of arc. A drill guide slide is maintained to slide along the arcuate slide track. The drill guide sleeve is to receive a drill tube or barrel fitted to be movable through the drill guide slide extending across the arcuate slide track, and aligns with a target point along the reference rod.

The drill tube or barrel is movable through the drill guide slide to contact a femur or tibia surface that is exposed by the surgeon/operator by opening the patient's skin, with the drill tube or barrel to receive a conventional drill turned therethrough that will pass into the bone and intersect a point along the reference rod, which reference rod is positioned in a femoral or tibial tunnel section. To provide for drilling a hole or passage to a selected location along a tunnel section that will be at an angle less than or greater than a right angle, the drill guide slide is moved along the arcuate slide track to an appropriate location therealong so as to form the selected angle into the tunnel section. Which angle of hole or passage is indicated by a particular scale marking whereover the drill guide slides, and involve a series of equal spaced scale markings formed along the arcuate slide track, with a center marking providing a right angle to the reference rod.

A depression is formed the in reference rod as the drilling target, which reference rod can be moved through the slide block and locked at an appropriate location. To provide for exactly hitting the target depression, a comparison is made with the position of the reference rod in the slide block as indicated by a slide block flat side or face that is aligned with a particular single marking of a number of spaced markings that are formed along the reference rod. To maintain the reference rod target depression as the center of radius of the arcuate slide track, such that a hole or passage will be drilled thereto, along with a movement to position the reference rod, the straight base leg is also moved through the slide block. The base leg is moved appropriately to shorten or lengthen the radius distance, which movement depends upon where the target depression is located along a tunnel section. Positioning of the straight base leg in the slide block is determined by an alignment of the slide block flat side or face over a particular marking of a number of spaced markings that are scribed along that straight base leg. In practice, the same number marking is selected on both the reference rod and straight base leg. With the distances between the selected markings is determined to maintain the required radial relationship of the drill tube or barrel to the target depression formed in the reference rod.

The drill guide of the invention can be fitted through either tunnel section open end to drill to a location along one at the tunnel sections, and can be pivoted around the tunnel section to drill from different points over the femoral or tibial surfaces so as to intersect that tunnel section. Further, the drill guide of the invention can be arranged to drill to one of a number of locations along either tunnel section. A hole or passage that is so drilled is to receive a fastener, such as a set screw, interference screw, or the like, turned therein for securing a ligament end in that tunnel section.

THE DRAWINGS

These and other objects and features of the invention in a variable angle drill guide will become more fully apparent from the following description in which the invention is described in detail in conjunction with the accompanying drawings.

DETAILED DESCRIPTION

Figure 1:
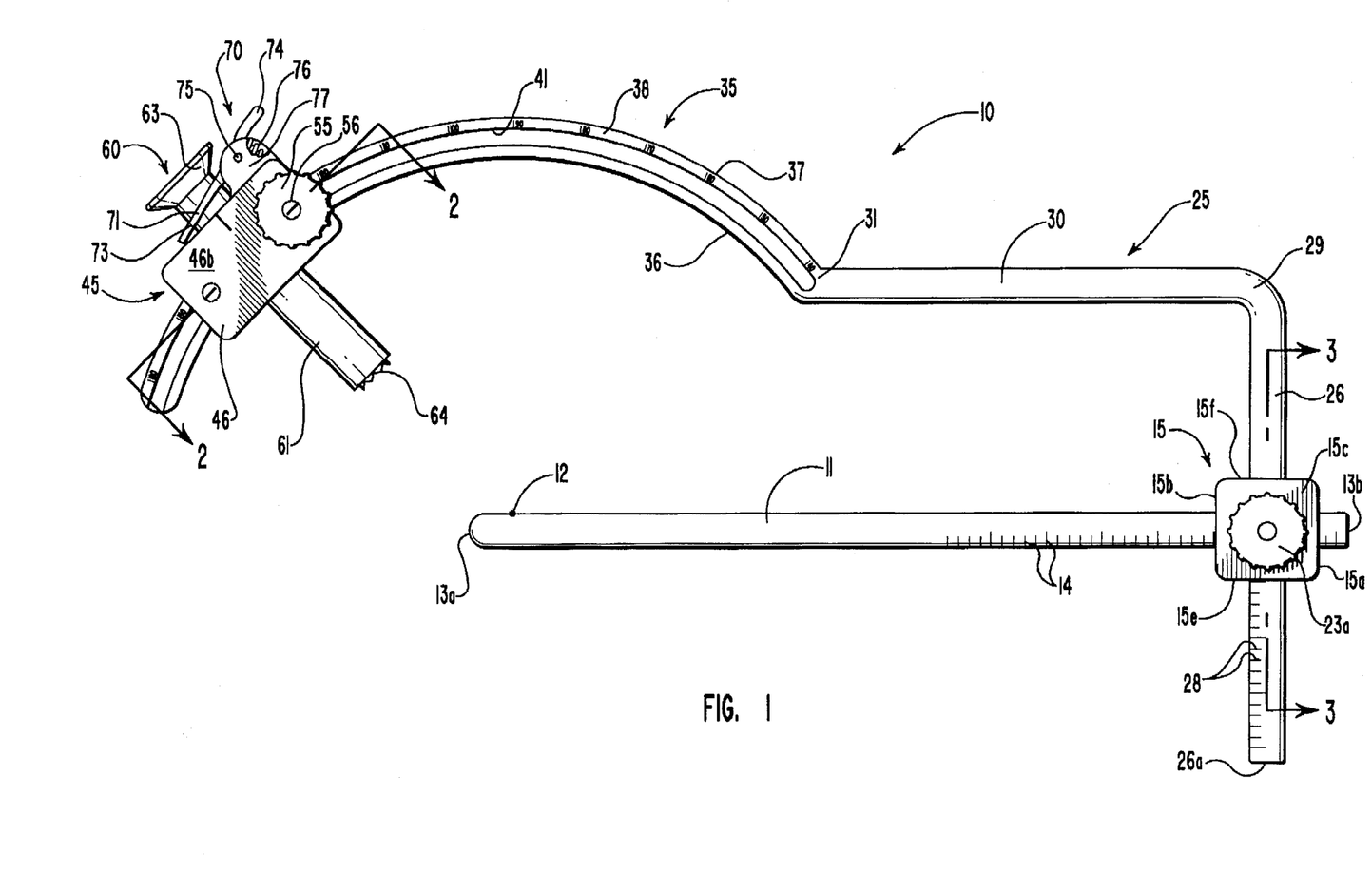
FIG. 1 is a front elevation view of the variable angle drill guide of the invention showing a guide barrel maintained and extending from a drill guide slide and is aligned with a target depression formed on a reference rod.
Figure 4:
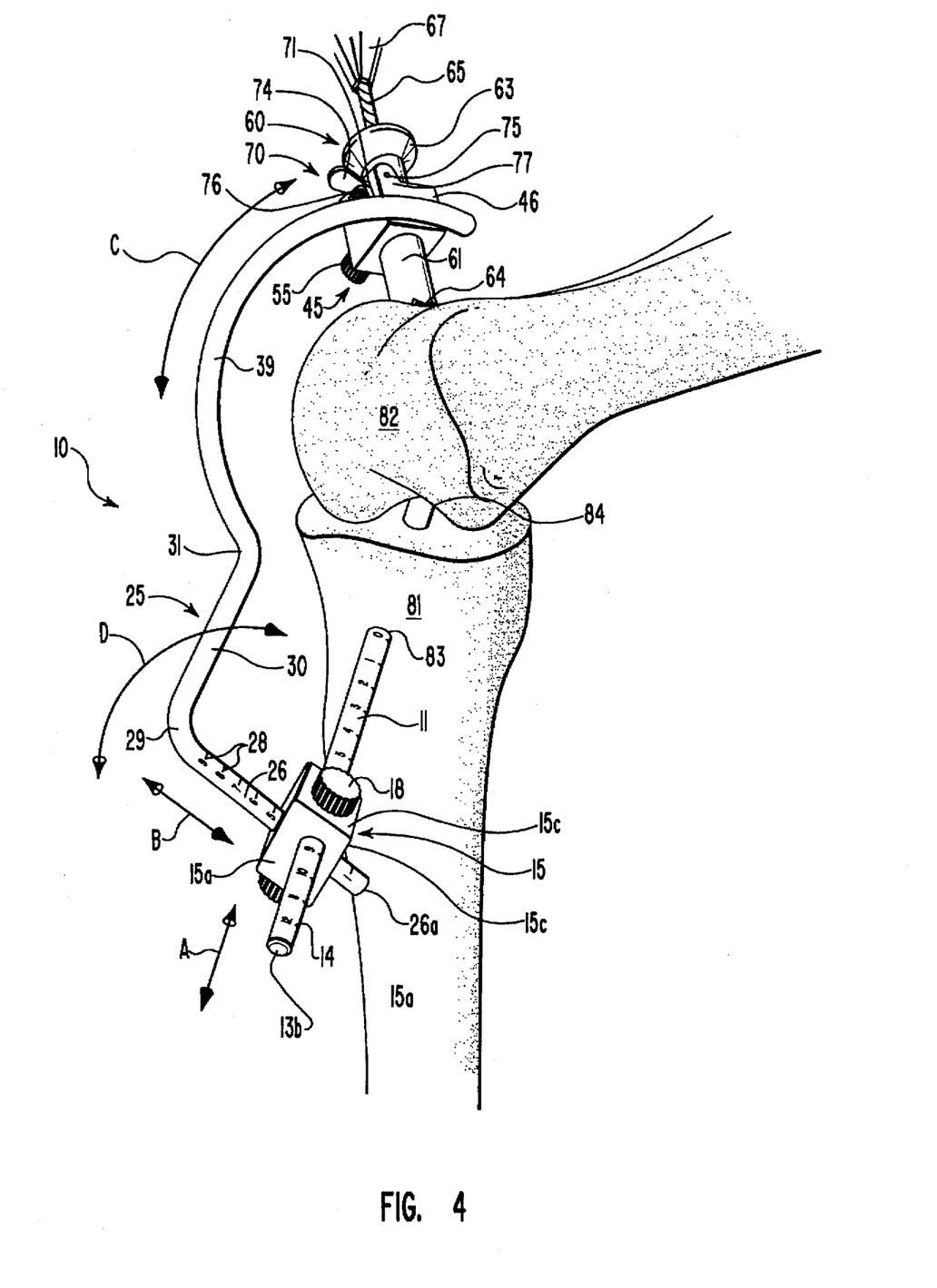
FIG. 4 is a side elevation perspective view of a patient's knee wherethrough femoral and tibial tunnel sections have been formed that are aligned into a straight tunnel and wherein the reference rod of the variable angle drill guide of FIG. 1 has been fitted through the tibial tunnel section end, and showing a drill guide slide positioned along an arcuate slide track, and with a drill fitted through a guide barrel thereof for turning into the distal femur to intersect a point along the femoral tunnel section at an angle that is greater or lesser than a right angle.
Figure 5:
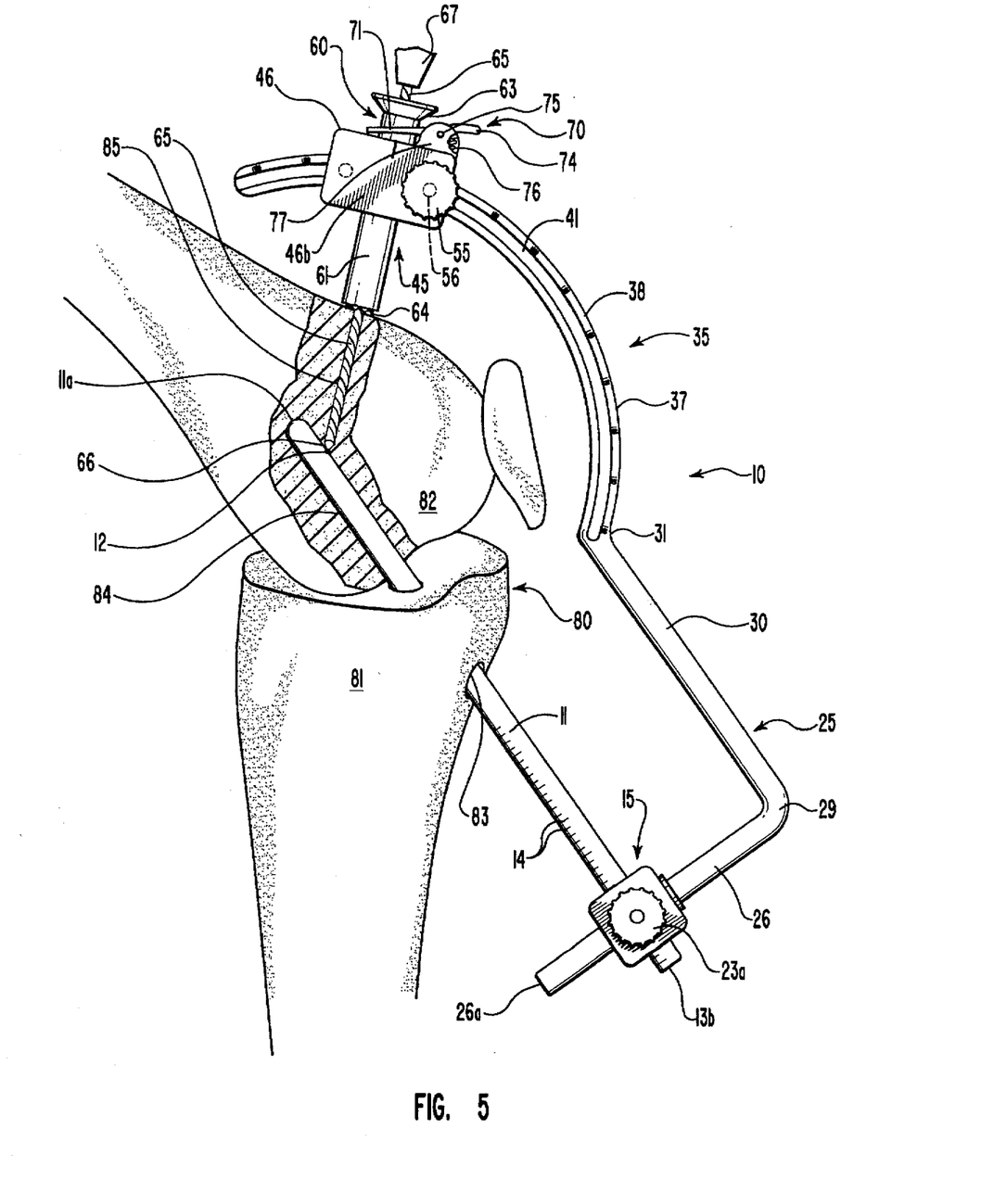
FIG. 5 is a side elevation view like that of FIG. 4 only showing the variable angle drill guide of FIG. 1 as having been pivoted across the knee that has had a section of the distal femur removed to show a drill turned through the guide barrel intersecting the femoral tunnel section and contacting the target depression on the reference rod at an angle greater than ninety (90) degrees.

FIG. 1 shows a front elevation view of a variable angle drill guide 10 of the invention, that is hereinafter referred to as drill guide. The drill guide 10 includes a straight reference rod 11 that, shown in FIGS. 1, 4 and 5, is preferably solid and has a round cross section. A target depression 12 is formed in the reference rod in FIG. 1 and is shown in FIG. 5 being contacted by a pointed end 66 of a drill 65. Which target depression 12 is spaced apart from a reference rod top end 13a and, in practice, is to serve as an aiming point for drill 65, as set out in detail hereinbelow.

Shown in FIGS. 1, 4 and 5, the reference rod 11 includes markings 14, that, as shown, are preferably lines identified with numbers scribed at spaced intervals therealong. The markings 14 are shown in FIG. 4 as beginning with a (twelve), that is proximate to a reference rod lower end 13b, and descending at equal intervals to (zero). Though, it should be understood other numbers, or other markings such as letters, could be so used within the scope of this disclosure.

Figure 3:
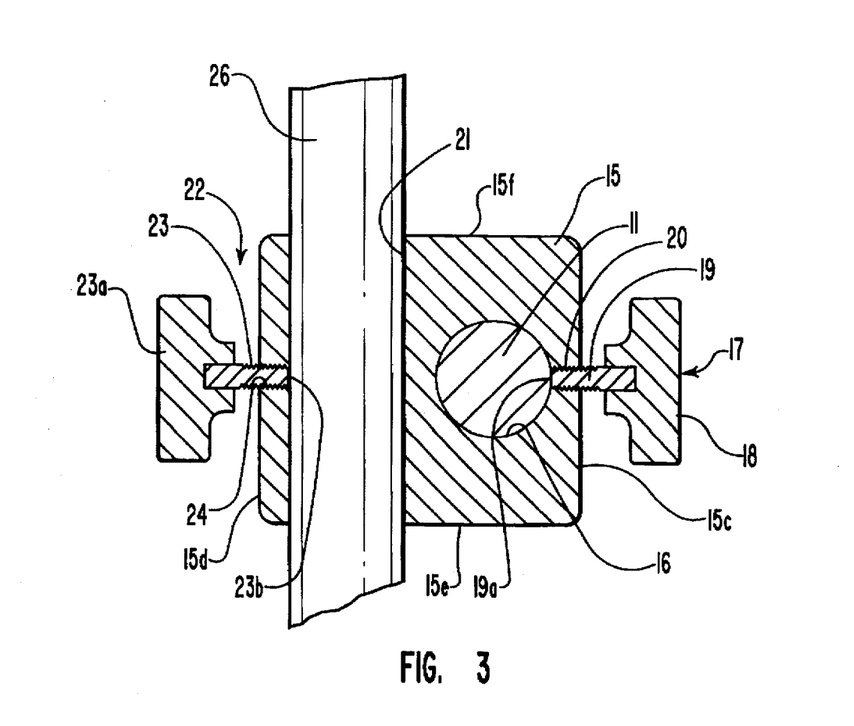
FIG. 3 is a sectional view of the slide block taken along the line 3—3 of FIG. 1 showing the reference rod and straight base leg of the variable angle drill guide fitted therethrough, with the slide block shown as including lock bolts for turning through the slide block into engagement with the respective reference rod and straight base leg for maintaining their positioning and orientation.

The reference rod end 13b is shown in FIGS. 1, 4, and 5 as having been fitted through a slide block 15 that has a rectangular shape, with edges that are at right angles to one another. The slide block 15, as shown in FIGS. 1, 4 and 5, and in cross section in FIG. 3, includes a straight horizontal hole 16, shown in FIG. 1 formed through block faces 15a and 15b, that is for receiving the reference rod 11 fitted to slide therein. For maintaining the alignment of the reference rod 11 and locking it in the slide block 15 hole 16, a bolt 17 is provided that includes a broad head end 18 and has a threaded body 19. The bolt threaded body 19 is turned into a threaded hole 20 formed through a slide block top 15c to where a body 19 end 19a intersects the straight horizontal hole 16 and engages the side of reference rod 11. So arranged, the reference rod 11 is locked in place.

The slide block 15, additional to accommodating reference rod 11 fitted to slide therethrough, includes a crossing hole 21 that is spaced a distance apart from the straight hole 16 and at a right angle. The crossing hole 21 is also straight and is formed through slide block faces 15e and 15f for accommodating a straight base leg 26 of a drill guide brace 25. The straight base leg 26 is preferably a solid rod. Like reference rod 11, straight base leg 26 is to be positioned to travel therein and can be locked in place in the crossing hole 21. Locking in place of the base leg is preferably accomplished by turning a threaded body 23 of a bolt 22, that has a broad head end 23a, into a threaded hole 24 formed through a face 15d of slide block 15. The bolt 22 is turned into threaded hole 24 to where a threaded body lower end 23b engages the side of base leg 26, locking the base leg 26 in the slide block 15, as shown.

The base leg 26, like the reference rod 11, as shown in FIGS. 1 and 4, includes spaced markings 28 formed therealong, from an end 26a, shown as a series of numbers starting with a number (twelve) that is adjacent to end 26a, and decreasing to (zero). The markings 28 are shown as numbers, but may be letters, or the like, within the scope of this disclosure. Also, as set out hereinbelow, markings 28 do not represent a same spacing distance as the distance between markings 14 that are scribed onto reference rod 11. The markings 14 and 28 spacing distances, however, will have the same number identifiers and are to be aligned with edges of the slide block 15 in the operation of the drill guide 10, as set out and described in detail later herein.

The drill guide brace 25, shown in FIGS. 1, 4 and 5, includes the straight base leg 26 that is bent at 29 through a right angle into a guide mounting leg 30. The guide mounting leg, at an upper or top end 31 connects to or is formed into an arcuate slide track 35 that includes equally spaced apart and identical inner and outer curved surfaces 36 and 37. Which arcuate slide track 35 and drill guide brace 25 are preferably secured together, arranged in the same plane. The arcuate slide track 35, as shown in FIGS. 1, 4 and 5, is uniformly curved into an arc of approximately one hundred twenty (120) degrees, and has spaced markings 40 scribed along a top surface 38 that represent degrees of arc therealong, with a center marking 40 identified as at ninety (90) degrees. At which ninety (90) degree marking 40, a drill passed across this marking would intersect the reference rod 11 at a right angle, and the markings 40 below and above which ninety (90) degree marking are at lesser or greater than ninety (90) degree angles to the reference rod 11.

Figure 2:
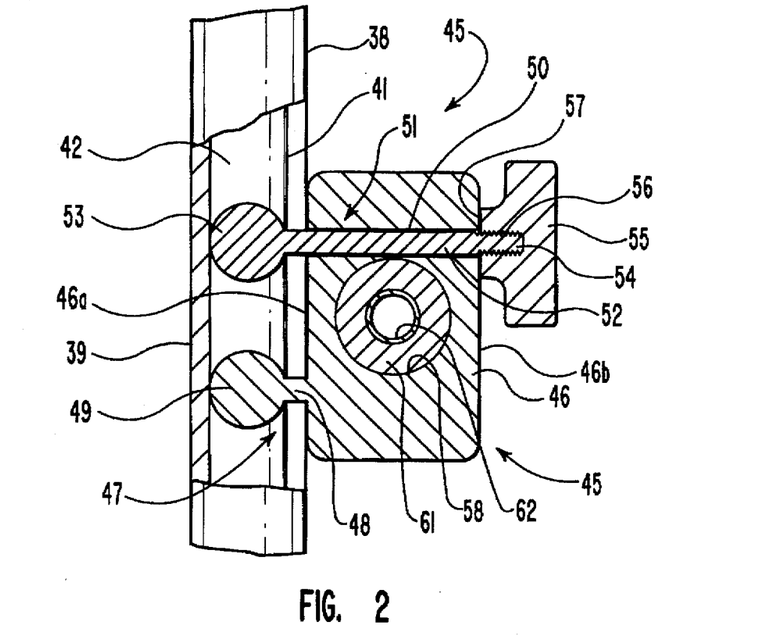
FIG. 2 is a sectional view of the drill guide slide taken along the line 2—2 of FIG. 1, showing ball feet of the drill guide slide fitted into an arcuate slot that is formed in an arcuate shaped slide track, showing a friction locking of one of which ball feet therein, and showing the drill guide barrel fitted therethrough.

Shown in FIGS. 1, 2 and 5, the arcuate slide track 35 includes top face 38, whereof spaced markings 40 are scribed, and has a parallel bottom face 39, shown in FIGS. 2 and 4. A slot 41 is shown in FIGS. 1 and 5 formed through the arcuate slide track top face 38 along the length thereof that, as shown in the cross section of FIG. 2, opens into a center passage 42. The center passage 42 has a greater diameter than the width of slot 41, and is open through at least one end and optionally both ends of the arcuate slide track. The slot 41 is to accommodate ball shaped end 49 of a fixed slide foot 47 and a ball shaped end 53 of a movable slide foot 51 of a drill guide slide 45. As shown in FIG. 2, the drill guide slide 45, is preferably a rectangular block 46 that has right angle corners and includes, extending from a forward portion of a bottom face 46a thereof, the fixed slide foot 47. Fixed slide foot 47, has a narrow body 48 and enlarges into a ball shaped end 49. For accommodating the movable slide foot 51, a straight passage 50 is shown in FIG. 2 formed through the block 46, from the bottom face 46a to a top face 46b thereof. The passage 50, as shown best in FIG. 2, receives a long straight rod shaped neck 52 of movable slide foot 51 fitted therethrough. The neck 52 mounts the ball 53 on a lower end thereof and is threaded at 54 along a top end portion. A cap nut 55, that includes a threaded center cavity 56, that is also shown in broken lines in FIGS. 1 and 5, is for turning onto the threaded end portion 53 of the slide foot 51. A surgeon/operator, by manually turning the cap nut 55, turns a cap nut lower face 57 into engagement with the block 46 top surface 46b. The slide foot 51 is thereby elevated so as to pull the ball 53 upper portion against the undersurface of the edges of the slot 41. This action locks the ball 53 and drill guide slide 45 to the arcuate slide track 35 top face 38.

Shown in FIG. 2, a smooth hole 58 is formed across the block 46 that is spaced apart from and crosses, at a right angle, the passage 50. The hole 58 is for receiving a body 61 of a guide barrel 60, that is shown in FIGS. 1, 2, 4 and 5, fitted therethrough. The body 61, shown best in FIG. 2, has a straight center longitudinal passage 62 formed therethrough, to guide a drill 65 that is mounted in to be turned by a chuck 67, as shown in FIGS. 4 and 5. To facilitate fitting a drill pointed end 66 into the passage 62, the body 61 may include a broad funnel shaped top end 63, and has a bottom or lower end that preferably includes serrations 64 formed therearound for gripping or biting into a bone surface, as shown in FIG. 5.

FIGS. 1, 2, 4 and 5, show the guide barrel 60 to preferably have a smooth outer surface for fitting to slide freely through the hole 58 that is formed through the drill guide slide 45. So arranged, once appropriately positioned for guiding drilling, as shown in FIGS. 4 and 5, it is necessary to maintain that guide barrel 60 positioning. Such barrel positioning, as shown in FIGS. 1, 4 and 5, and best in FIGS. 1 and 5, is provided by a friction arm 70. The friction arm 70 includes a plate 71 that has a broad flat forward end 72 wherethrough a hole 73, shown in broken lines in FIG. 1, is formed. The hole 73 is formed to just accommodate the guide barrel cylindrical body 61 fitted therethrough. The plate 71 tapers inwardly from its forward end 72 a thumb engaging curved rear end 74, and is pivotally mounted at pivot 75 between parallel braces 77. A spring 76 is positioned beneath the rear end 74 and the guide body 61 surface, to provide a spring biasing that urges the rear end 74 upwardly, away from the guide body 61. So arranged, a surgeon/operator depresses the plate 71 rear end 74 against the biasing of spring 76 elevates the plate forward end 72, aligning the hole 73 with the guide barrel outer wall. This allows the guide barrel 60 to freely move up or down within the hole 58 to a desired guide barrel position. Whereafter, by releasing pressure on the rear end 74, the plate forward end 72 is pivoted downwardly with the edges of hole 73 engaging the surface of the guide barrel body 61, locking it in place.

Hereinabove has been set out a preferred movable mounting of the guide barrel 60 in the drill guide slide 45, it should, however, be understood that other arrangements for allowing for an adjustment of guide barrel 61 positioning and its locking at that selected position could be so used within the scope of this disclosure. For example, another such arrangement could be forming threads along the guide barrel surface for turning in hole 58 that has been threaded.

Shown in FIG. 4, the reference rod 11 can be moved through the slide block 15, as indicated by arrow A, to shift the positioning of the reference rod target depression 12, as shown in FIGS. 1 and 5. Which repositioning of the reference rod 11 through hole 16 moves a different numbered marking 14 into alignment with a reference edge of slide block 15, such as face 15b. To maintain a positioning of the guide barrel 60 fitted through the drill guide slide 45 to appropriately point at the target depression 12, as the reference rod 11 is moved through the slide block 15, the straight base leg 26 needs to be moved through the slide block crossing hole 21, as illustrated by arrow B. In which movement, the straight base leg 26 is repositioned such that a different marking 28 is aligned with the base leg reference edge to the slide block 15, such as a slide block face 15f. Which reference rod and base leg reference edges or faces are at right angles to one another, and each of the selected single marking of markings 14 and 28 will be identified by the same number, thereby maintaining the guide barrel 60 pointed at the target depression 12 formed in reference rod 11. While the same numbering is selected as the marking of markings 14 and 28, it is necessary that the distance between the markings 14 be different from the distance between markings 28 to maintain required center of radius relationship of the center of the drill guide slide 45, through which center the guide barrel 60 is fitted. So arranged, the guide barrel 60 will continuously point at the target depression 12 as the drill guide slide 45 is moved along the arcuate slide track 35, illustrated by arrow C.

Figure 6:
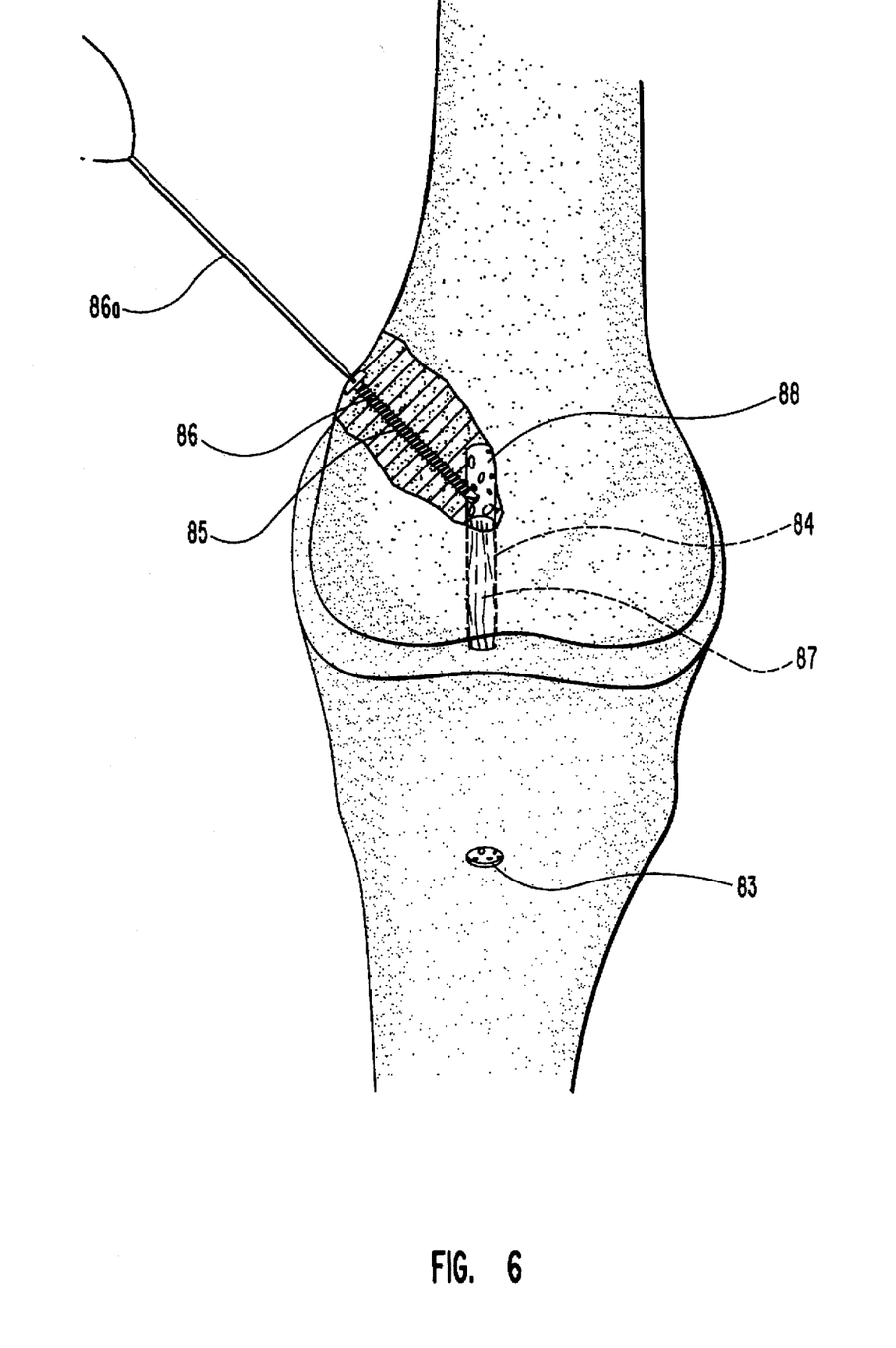
FIG. 6 is a frontal elevation view of the knee of FIGS. 4 and 5 showing a passage as having been formed into the side of the knee that is at an angle greater than ninety (90) degrees and showing a screw being turned into that formed passage to engage a bone end of a bone tendon bone ligament graft fitted therein.

In practice, a surgeon/operator performing a surgical procedure on a patient's knee 80, as shown in FIGS. 4, 5 and 6, wherein straight tunnel sections have been formed in their proximal tibial 81 and distal femur 82, the surgeon/operator first fits, as shown, the reference rod 11 of the drill guide 10, into a tibial tunnel end 83 of straight tunnel 84. Which straight tunnel 84 is formed by aligning femoral and tibial tunnel sections that have been formed into the patient's tibia and femur. While the reference rod is shown fitted into the tibial tunnel end for use in forming a passage 85, for intersecting the femoral tunnel section, it should be understood within the scope of this disclosure that the drill guide 10 could be turned and the reference rod 11 fitted into a femoral tunnel section end to form a passage to intersect either the tibial or femoral tunnel section.

Further, FIGS. 5 and 6 show passages 85 that have been formed from different locations on the femur 82 cortex surface to intersect the femoral tunnel section, for illustrating the versatility of the drill guide 10. For such passage drilling, the surgeon/operator can pivot the drill guide brace 25 that mounts the arcuate slide track 35 to where the guide barrel 60 that is fitted through the drill guide slide 45 is pointed at a location on the distal femur or proximal tibial surface that the surgeon/operator determines to drill through to hit the target depression 12 on the reference rod. Which point on the bone cortex is selected to avoid damage to knee ligaments, muscles, or the like. Along with a selection of a point or location to drill from, the surgeon/operator will select an angle and set same, by appropriately moving the drill guide slide 45, as shown in FIGS. 4 and 5. The angle section will take into account the knee anatomy and will provide a bone thickness to a fastener to be fitted therein so as to maximize the purchase. A fastener, shown as a screw 86, is then turned into passage 85 utilizing a screw driver 86a, shown in FIG. 6. The screw 86 that is turned through the passage 85, as shown in FIG. 6, is to intersect a ligament graft 87 that has been fitted in the femoral section of the straight tunnel, and is to secure the graft end 88 therein. The ligament graft 87 is shown herein as a bone tendon bone graft, with the screw 86 for providing an endosteal mounting of that ligament graft. Accordingly, the drill guide of the invention allows the surgeon/operator to select a point along a tunnel section, that is either a tibial or femoral tunnel section, to form passage 85 from a point or location on the bone surface at a selected angle to the point or location along the tunnel section. This is accomplished by an appropriate setting of the reference rod target depression 12 at the selected tunnel section location and by reconfiguring the reference rod 11 and straight base leg 26 positioning in the slide block 15 to maintain the guide barrel on a radial to the target depression.

A preferred embodiment of the present invention in a variable angle drill guide and a method for its use has been shown and described herein. It should, however, be understood that this disclosure is made by way of example only and that variations and modification to the described device and its use are possible without departing from the subject matter coming within the scope of the following claims and a reasonable equivalency thereof, which claims we regard as our invention.

We claim:

1. A variable angle drill guide comprising;
    a straight reference rod having a first end for sliding engagement with a ligament tunnel in a bone and an opposite second end that is arranged to be fitted into a first passage formed through a slide block means;
    a slide block means that includes straight first and second passages therethrough, with said second passage spaced from said first passage;
    a straight base leg rod section of a drill guide brace that is arranged to be fitted into said second passage and includes a straight drill guide mounting leg section connected at a first end to said base leg rod section and further connected at an opposite second end to a slide track means;
    a slide track means formed with a uniform arcuate shape for mounting a drill guide slide fitted with a drill guide barrel thereon, said slide track means having spaced apart markings for identifying a range of selected angular orientations formed between a longitudinal axis of said drill guide barrel and a longitudinal axis of said reference rod, said range including angular orientations of both less than and greater than a right angle;
    a drill guide slide that is fitted to receive a drill guide barrel and that is arranged for sliding engagement with said slide track means; and
    a drill guide barrel having a straight longitudinal passage formed therethrough and including means for releasable mounting to said drill guide slide.

2. A variable angle drill guide as recited in claim 1, wherein the first and second passages formed through the slide block means are at right angles to one another; and the drill guide mounting leg section is connected at a right angle to the base leg rod section.

3. A variable angle drill guide as recited in claim 1, further including a target depression formed in the first end of said reference rod and markings are scribed at spaced intervals along portions of said second end of said reference rod and the base leg rod section that, when said reference rod and base leg rod section are fitted through the slide block means, are for aligning with indicator means arranged with said slide block means to indicate a corresponding relationship between said reference rod and said base leg rod section whereby said target depression may be accurately placed to intersect said longitudinal axis of said drill guide barrel.

4. A variable angle drill guide as recited in claim 3, further including means for releasably locking the reference rod and base leg rod section in the slide block means.

5. A variable angle drill guide as recited in claim 1, wherein the slide track means is an arcuate segment having an arcuate length corresponding to approximately 120 degrees of arc and having parallel top and bottom surfaces, said top surface including spaced marking scribed thereacross that are numbered to represent degrees of arc, said numbered markings including a 90 degree marking at a midpoint along said top surface which corresponds to a location at which said drill guide slide with said drill guide barrel may be placed so that the longitudinal axis of said drill guide barrel is configured to form a right angle with the longitudinal axis of said reference rod.

6. A variable angle drill guide as recited in claim 5, further including a longitudinal slot formed in the slide track means top face and along the arcuate length of said slide track means; and slide means extending from an undersurface of the drill guide slide that is arranged for fitting into said longitudinal slot so as to slide along said longitudinal slot.

7. A variable angle drill guide as recited in claim 6, wherein the slide means is a fixed ball end formed onto a lower end of a straight fixed stem whose upper end is secured, at approximately a right angle, to an undersurface of the drill guide slide; a movable ball end of a movable stem fitted so as to be movable up and down in a passage formed through said drill guide slide, and means for lifting said stem and attached movable ball end within the longitudinal slot to lift said movable ball end into engagement with the undersurface of edges of said longitudinal slot; and means for moving said movable stem along said drill guide slide.

8. A variable angle drill guide as recited in claim 1, further including means for extending and locking in place the drill guide barrel through the drill guide slide.

9. A variable angle drill guide as recited in claim 8, wherein the means for extending and locking the drill guide barrel includes a friction arm means that is pivotally connected to the drill guide slide to be moved by an operator/surgeon for engaging the drill guide barrel and maintaining until released its positioning at a location along said drill guide slide.

10. A variable angle drill guide as recited in claim 9, wherein the friction arm means includes an arm that is pivotally mounted to the drill guide slide and has an edge for engaging and binding against a surface of the drill guide barrel; and said arm is spring biased into engagement with said surface of said drill guide barrel, which said spring biasing is arranged to be overcome by a surgeon/operator depressing a tab end of said arm so as to pivot said arm edge out of engagement with said surface of said guide barrel.

11. A variable angle drill guide as recited in claim 1, wherein the drill guide barrel includes a funnel shaped end fixed on a top end, and includes serrations formed on a bottom end.

12. A method for mounting an end of a ligament graft in a prepared tunnel section of a ligament tunnel that has been formed in a patient's distal femur and proximal tibia, the method comprising the steps of:

selecting a location along the ligament tunnel for placement of a screw fixation hole, said location selected to provide sufficient bone mass for anchoring a graft fixation screw;

providing a variable angle drill guide comprising: a reference rod having a first end including a target depression and an opposite second end including indicia markings; a slide block means having straight first and second passages therethrough, said first passage configured for sliding engagement with said reference rod and said second passage configured for sliding engagement with a base leg rod section; a straight base leg rod section having indicia markings; a straight drill guide mounting leg section connected at a first end to said base leg rod section and further connected at a second opposite end to a slide track means; an arcuately shaped slide track means having indicia markings which represent degrees of arc; a drill guide slide configured for sliding engagement with said slide track means; a drill guide barrel configured for sliding engagement with said drill guide slide, said drill guide barrel having a bone engagement end and an opposite drill entry end;

sliding the first end of the reference rod into the ligament tunnel;

sliding the slide block means onto the second end of the reference rod, through the first passage in the slide block means, and to a selected indicia marking;

sliding the base leg rod section into the second passage in the slide block means and adjusting the position of the base leg rod section to a selected indicia marking which corresponds to the previously selected indicia marking of the reference rod, resulting in a correct positioning of the slide track means;

sliding the drill guide slide onto and along said slide track means and adjusting the position of the drill guide slide to a selected indicia marking which corresponds to the previously selected indicia markings of the reference rod and the base leg rod section;

mounting the drill guide barrel into and sufficiently through the drill guide slide to place the bone engagement end against a bone surface;

turning a drill through said drill guide barrel to form a screw fixation hole at the selected location, said drill meeting the target depression on the end of the reference rod in the ligament tunnel;

removing the drill from the drill guide barrel;

removing the reference rod from the ligament tunnel;

fitting a ligament graft into the ligament tunnel; and screwing a graft fixation screw into the screw fixation hole to a sufficient depth to allow an end of a graft fixation screw to fix an end of a ligament graft in the ligament tunnel.

13. A method as recited in claim 12, further comprising the step of after sliding the slide block means onto the reference rod step, releaseably locking the reference rod in first passage in the slide block means.

14. A method as recited in claim 13, further comprising the step of after sliding the base leg rod section into the second passage in the slide block means step, releasably locking the base leg rod section in the slide block means.

15. A method as recited in claim 14, further comprising the step of after mounting the drill guide barrel step, releasably locking the drill guide slide on the slide track means and releasably locking the drill guide barrel in the drill guide slide.

* * * * *